(12) United States Patent
Bauss et al.

(10) Patent No.: US 11,432,904 B2
(45) Date of Patent: Sep. 6, 2022

(54) RFID TAG ENABLED NEEDLE SHIELD

(71) Applicant: SHL MEDICAL AG, Zug (CH)

(72) Inventors: Markus Bauss, Lengdorf (DE); Thomas Dietl, Farkenfels (DE)

(73) Assignee: SHL MEDICAL AG, Zug (CH)

( * ) Notice: Subject to any disclaimer, the term of this patent is extended or adjusted under 35 U.S.C. 154(b) by 101 days.

(21) Appl. No.: 17/095,006

(22) Filed: Nov. 11, 2020

(65) Prior Publication Data

US 2021/0068919 A1      Mar. 11, 2021

Related U.S. Application Data

(60) Continuation of application No. 16/871,893, filed on May 11, 2020, now Pat. No. 10,864,059, which is a
(Continued)

(30) Foreign Application Priority Data

Jul. 11, 2016   (EP) ..................... 16178833

(51) Int. Cl.
*A61M 5/31*         (2006.01)
*A61B 90/98*        (2016.01)
(Continued)

(52) U.S. Cl.
CPC .............. *A61B 90/98* (2016.02); *A61M 5/31* (2013.01); *A61M 5/3129* (2013.01);
(Continued)

(58) Field of Classification Search
CPC ...... A61M 39/20; A61M 5/31; A61M 5/3129; A61M 2205/60; A61B 90/98
See application file for complete search history.

(56) References Cited

U.S. PATENT DOCUMENTS

2006/0230276 A1   10/2006   Nochta
2007/0239112 A1   10/2007   Fago et al.
(Continued)

FOREIGN PATENT DOCUMENTS

CN      101304775 A     11/2008
CN      100553582 C     10/2009
(Continued)

*Primary Examiner* — Benyam Haile
(74) *Attorney, Agent, or Firm* — McDonnell Boehnen Hulbert & Berghoff LLP

(57) ABSTRACT

The present invention relates to an RDID tag enabled needle shield assembly that provides a sterile enclosure of an injection needle and that can be fixedly attached to a pre-filled syringe for administering an injection of medicament to a patient after removal of the needle shield assembly. The RFID tag is fixedly attached to the needle shield through co-molding or another form of permanent attachment. The present invention also relates to a method of tracking the life cycle of a medicament injection device where the RFID tag enabled needle shield assembly is attached to an injection needle that is connected to a syringe barrel that is part of an injection device. Data is written to or read from the RFID tag during the entire life cycle of the injection device, including assembly, packaging, storing, distribution and use.

14 Claims, 8 Drawing Sheets

Related U.S. Application Data division of application No. 16/311,545, filed as application No. PCT/EP2017/065367 on Jun. 22, 2017, now Pat. No. 10,675,123.

(51) Int. Cl.
*A61M 5/32* (2006.01)
*G06K 19/077* (2006.01)
*A61M 39/20* (2006.01)

(52) U.S. Cl.
CPC ..... A61M 5/3202 (2013.01); G06K 19/07749 (2013.01); *A61M 39/20* (2013.01); *A61M 2005/3131* (2013.01); *A61M 2205/60* (2013.01)

(56) References Cited

U.S. PATENT DOCUMENTS

| | | |
|---|---|---|
| 2008/0191013 A1 | 8/2008 | Liberatore |
| 2008/0200747 A1 | 8/2008 | Wagner et al. |
| 2009/0043253 A1 | 2/2009 | Podaima |
| 2009/0306620 A1 | 12/2009 | Thilly et al. |
| 2012/0103140 A1 | 5/2012 | Kessler et al. |
| 2013/0072879 A1 | 3/2013 | Avery et al. |
| 2014/0223862 A1 | 8/2014 | Nicoletti et al. |
| 2014/0336588 A1 | 11/2014 | McLoughlin et al. |
| 2015/0080810 A1 | 3/2015 | Henderson et al. |
| 2015/0165135 A1* | 6/2015 | McLoughlin ....... A61M 5/5086 604/111 |
| 2015/0174338 A1 | 6/2015 | Takemoto |
| 2015/0314077 A1 | 11/2015 | Karlsson et al. |
| 2016/0022539 A1 | 1/2016 | Daines |
| 2016/0089530 A1 | 3/2016 | Sathe |
| 2016/0144132 A1 | 5/2016 | Scanlon |
| 2016/0175539 A1 | 6/2016 | Riedel et al. |
| 2016/0271336 A1 | 9/2016 | Thomsen |

FOREIGN PATENT DOCUMENTS

| | | |
|---|---|---|
| CN | 102847209 A | 1/2013 |
| CN | 102968724 A | 3/2013 |
| CN | 103608055 A | 2/2014 |
| CN | 104010678 A | 8/2014 |
| CN | 104379195 A | 2/2015 |
| CN | 105530980 A | 4/2016 |
| JP | 2008-535569 A | 9/2008 |
| JP | 2010-540054 A | 12/2010 |
| JP | 2014-514120 A | 6/2014 |
| JP | 2015514524 A | 5/2015 |
| TW | 201509474 A | 3/2015 |
| WO | 2006/108026 A2 | 10/2006 |
| WO | 2009/040601 A1 | 4/2009 |
| WO | 2012/152628 A1 | 11/2012 |
| WO | 2012/164390 A2 | 12/2012 |
| WO | 2013/160152 A1 | 10/2013 |
| WO | 2014075685 A2 | 5/2014 |
| WO | 2015/110533 A2 | 7/2015 |

\* cited by examiner

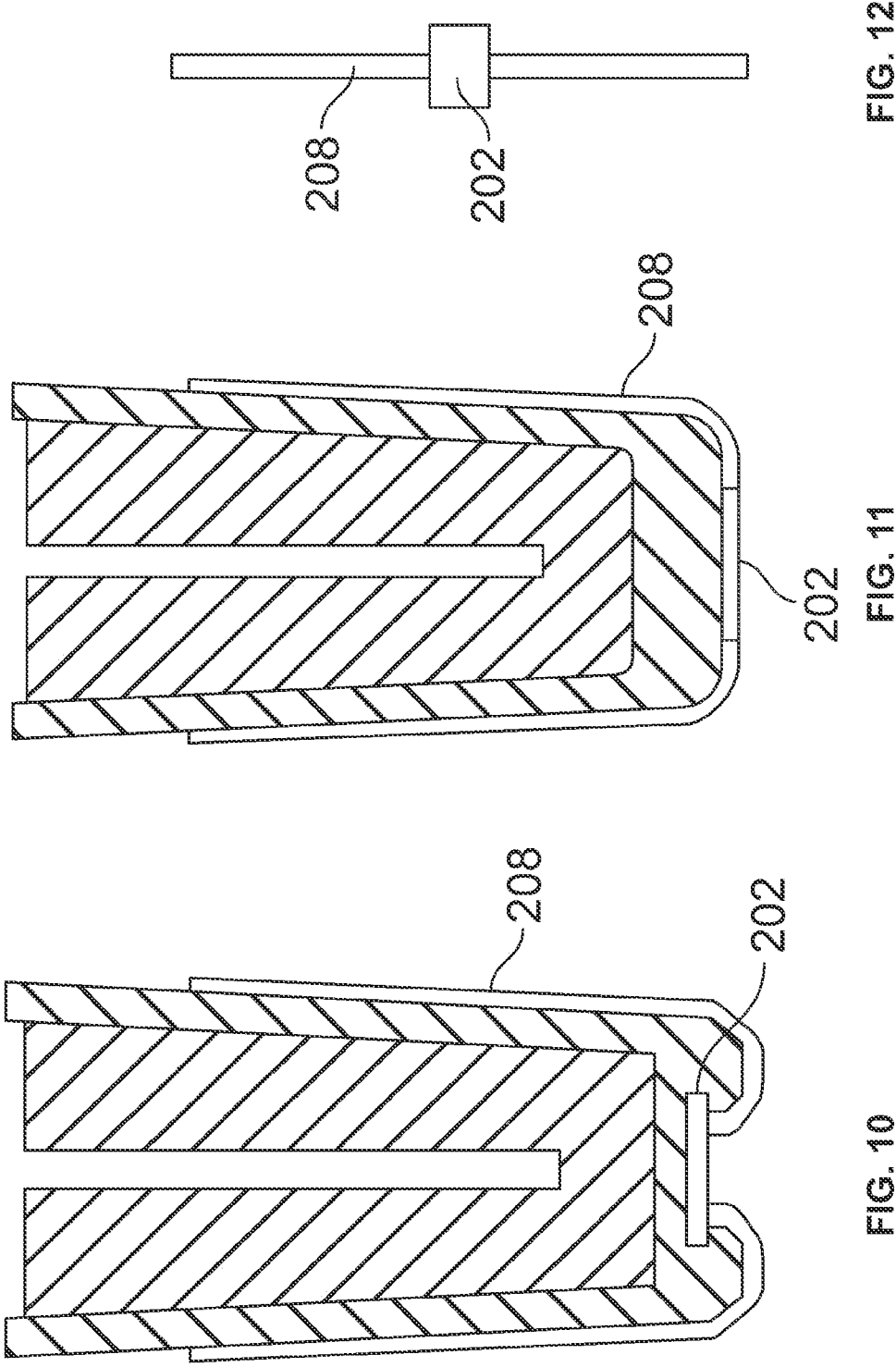

RFID TAG ENABLED NEEDLE SHIELD

CROSS REFERENCE TO RELATED APPLICATIONS

The present application is a continuation of U.S. patent application Ser. No. 16/871,893, filed May 11, 2020, which is a divisional of U.S. patent application Ser. No. 16/311,545, filed Dec. 19, 2018, now U.S. Pat. No. 1,067,512, which is a U.S. National Phase Application pursuant to 35 U.S.C. § 371 of International Application No. PCT/EP2017/065367 filed Jun. 22, 2017, which claims priority to European Patent Application No. 16178833.6, filed Jul. 11, 2016. The entire disclosure contents of these applications are herewith incorporated by reference into the present application.

FIELD OF THE DISCLOSURE

The present invention relates to the use of RFID tags in medical devices, more specifically an RFID tag incorporated into or attached to a needle shield assembly of an injection device. Such an RFID tag enabled needle shield can be useful in tracking the product life cycle, including the manufacturing, assembly, and distribution histories of an injection device designed to deliver one or more doses of a medicament.

BACKGROUND

In the areas of medical device design, manufacture, assembly, distribution and sale of medical devices, it has become important to have the ability to track the history of individual devices or lots of devices from early in the manufacturing life through to the end use of the device. For injection devices, such as auto-injectors, traceability and connectivity of the injection devices, as well as data recording and retrieving, is becoming the norm. Such a data carrier system should be integral with medical devices, preferably starting with a component of the device that represents the very beginning of the manufacturing or product life cycle. For example, the use of RFID tags (chips) should allow data writing and data reading through the entire history of the medical device, including data from the pharmaceutical manufacturer, the fill/finish process, the device assembly steps, the distribution centers, all the way through to the end user, the health care providers and patients. With incorporation of an RFID tag into such a device component, product and process and event history that builds up over the history of the device can be stored like a pedigree on the device itself without the requirement to store the relevant information in a separate or remote data-base, that requires access to information from each of the different parties involved with the manufacture, distribution and use of the device.

Such a tracking system is also useful in device quality control whereby specific physical, mechanical and chemical criteria are met, to ensure proper mechanical function of the device. In the case of injection devices, this includes criteria that arise during the syringe manufacturing process as well as during the device manufacturing, filling and packaging/assembly process. Having quality control data written to and read from individual devices will minimize scrap rates thus reducing the loss associated with expensive medicaments that are pre-filled into such devices. In the case of quality complaints from end users regarding specific components of the device or the entire final device itself, sometimes it is not easy, to clearly identify the root cause and have at the same time traceability to identify the relevant products based on additional information that is linked to each product.

In light of the above desires and goals relating to injection devices there exists a need for providing a single solution that allows tracking of an injection device. The present invention satisfies these goals and needs by providing an RFID tag enabled needle shield assembly that stays with the device from the beginning of the manufacturing process right up to the moment before a user begins an injection of medicament. Other benefits and objectives of the invention will become evident from the following more detailed description and included drawings.

SUMMARY

One primary purpose of the present invention is to provide a needle shield assembly that provides a sterile enclosure of an injection needle or other medicament delivery port that is fixedly attached to a pre-filled syringe or other container configured to hold one or more doses of a medicament, e.g., a drug. The needle shield assembly comprises an interior portion fabricated from a material that forms a sterile and fluid tight seal with a distal end of the injection needle or medicament exit port. Fixedly attached to the needle shield is an RFID tag that is configured as a read-write device that can store data throughout the product life cycle and can be read by an RFID reader as often as needed throughout the product life cycle. In some cases, it may be beneficial that the RFID tag be a read-only having a memory that contains only unique product identification data.

The needle shield assembly can further comprise a rigid outer cover and a soft inner cover, where the rigid outer cover is attached to the soft cover such that axial movement of rigid outer cover causes axial movement of the soft inner cover. In some cases, the RFID tag is preferably fixedly attached to the rigid outer cover. This can be achieved by one of a variety of fasteners, for example, a snap fit, an inlay, co-molding, an adhesive, lamination, tape, a press fit or a combination of any of these attachment methods. The needle shield assembly can also have an antenna in electrical communication with the RFID tag.

The needle shield assembly can be part of entire complete injection device, where the needle shield assembly is attached to a medicament container that is incorporated into a completely assembled injection device, such as a pen-type injector, an auto-injector that uses a pre-filled syringe, an infusion pump delivery system, or a patch type device. The injection device can itself have one or more RFID tags associated with one or more components of the device in addition to the RFID tag enabled needle shield assembly. These additional RFID tags can be configured to exchange information with the RFID tag attached to the needle shield assembly.

Another aspect of the invention relates to methods of tracking the life cycle of a medicament container comprising the RFID tag enabled needle shield assembly or the injection device incorporating the needle shield assembly from a point in time where the RFID tag is attached to a needle shield and the assembly is then removably attached an injection needle connected to a medicament container, such as a syringe barrel, to form a sterile and fluid tight seal with a distal end of the injection needle. Data is read from or written to this RFID tag as the medicament container moves through multiple manufacturing processes, such as, siliconization, medicament filling, shipping, quality control testing, warehousing, incorporation with or in other components to make a complete injection device.

These, as well as other, advantages of the various aspects of the RFID tag enabled needle shield, and the manner of attaining them, will become apparent to those of ordinary skill in the art by reading the following detailed description, with appropriate reference to the accompanying drawings.

BRIEF DESCRIPTION OF THE FIGURES

The invention will now be described in more detail and with reference to the appended drawings in which:

FIG. 10 is a cross-sectional view of a schematic representation of an embodiment of the RFID tag enabled needle shield assembly having an antenna of the present disclosure;

FIG. 11 is a cross-sectional view of a schematic representation of an embodiment of the RFID tag enabled needle shield assembly having an antenna of the present disclosure;

FIG. 12 is a schematic representation of an embodiment of an RFID tag and antenna combination of the present disclosure.

DETAILED DESCRIPTION

Figure 1:
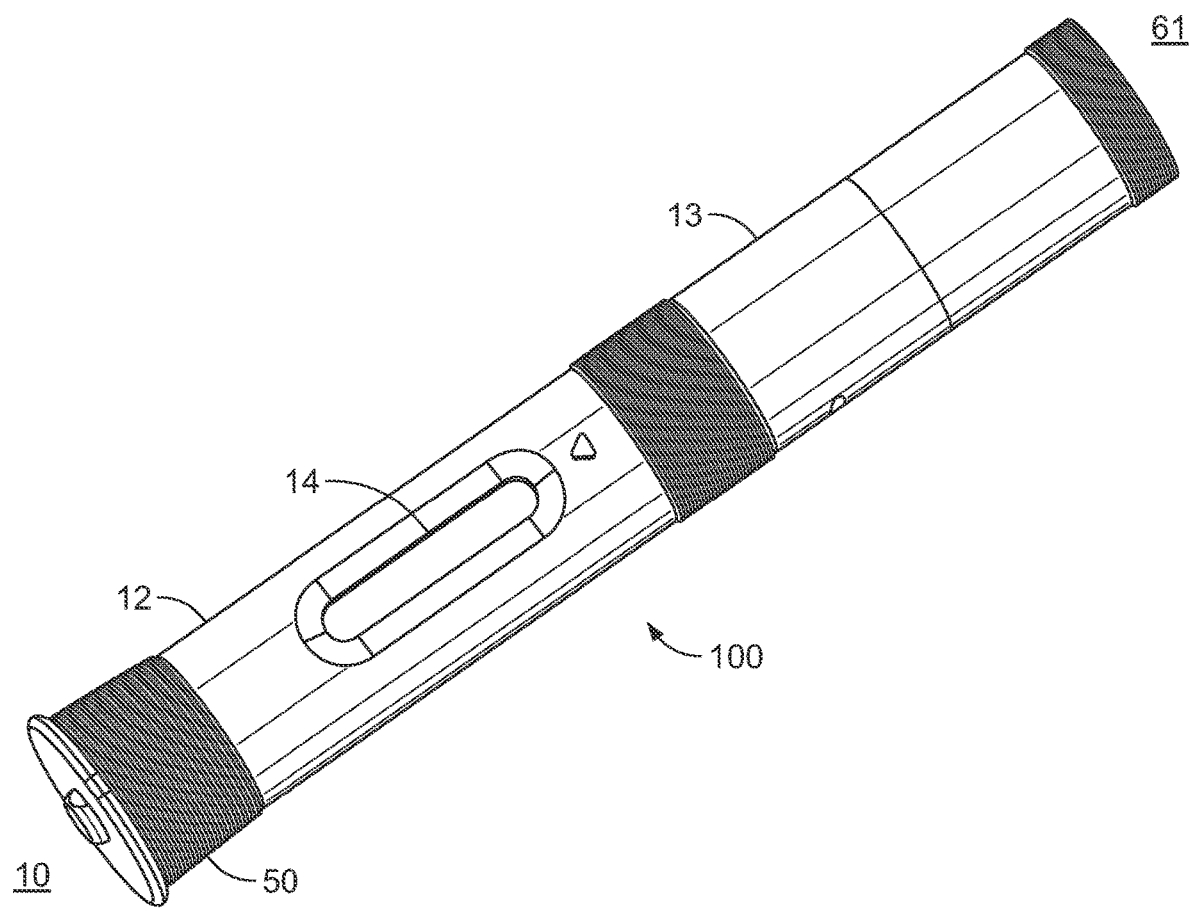
FIG. 1 is a perspective view of the drug delivery device of one embodiment of the present disclosure.

The ability to track the history or product life cycle of a medical device from the early beginnings of the manufacturing and assembly of the device through to its ultimate end use, while also having the ability to read and write data to the device throughout that history is an important benefit in assuring that only high quality and safe medical devices reach the ultimate end users. In the field of injection devices, particularly those that utilize pre-filled syringes containing medicaments, it has been found that the incorporation of an RFID tag into a single device component that is assembled as part of the device or a portion of the device early in its history will provide an accurate tracking or traceability of a specific device or particular lots of devices. Typically, injection devices are comprised of a main housing that encloses the mechanism for the setting a dose of medicament and/or for delivering a dose of medicament contained in a separate container within the main housing or attached to the main housing. FIG. 1 illustrates one example of an injection device that can be used in my invention. This particular injection device is an auto-injector.

Figure 2:
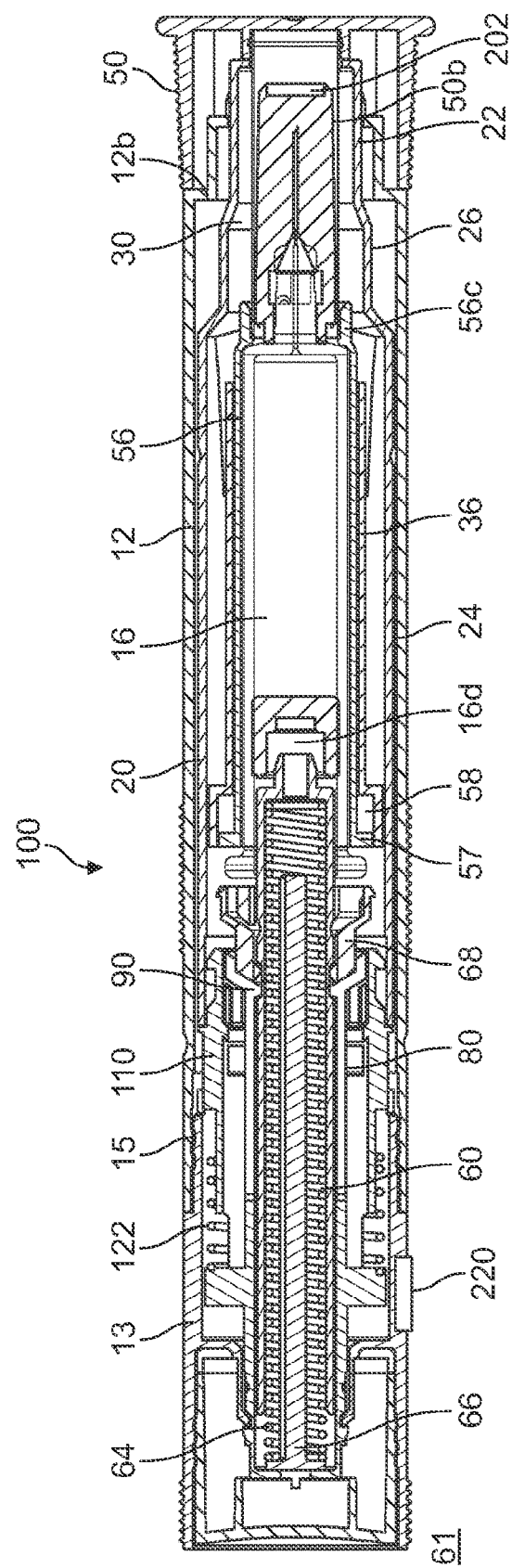
FIG. 2 is a cross-sectional view of the drug delivery device according to FIG. 1 showing an embodiment of the RFID tag enabled needle shield assembly of the present disclosure.

The drug delivery device 100 shown in the drawings comprises a front or proximal end 10 and a rear or distal end 61. The front end 10 comprises a generally tubular front body 12 having elongated openings 14 for viewing a syringe 16 as shown in FIGS. 1 and 2 and having a somewhat narrowing front end 12a (see FIG. 3). The rear end 61 of device 100 has a rear tubular rear body 13 that is joined with front body 12 with connection 15 (see FIG. 2), where one part of the connection 15 is on the front body 12 and the cooperating and mating connector is on the rear body 13. Inside the front body 12 is a needle shield 20 that is axially slidably arranged. The needle shield 20 is generally tubular with a first front part 22 having a certain diameter and a second rear part 24 having a diameter larger than the front part 22, where these parts are joined by an intermediate conical part 26. Two elongated grooves 28 are arranged along the needle shield 20, on opposite sides of the needle shield 20, also for viewing the syringe and guiding axial movement of the outer body 57. On the inner surface of the conical part 26 a circumferential ledge 30 is arranged. At the rear end of the needle shield 20 two openings 32 are arranged opposite each other, where each opening 32 is arranged with somewhat inwardly projecting, flexible, tongues 34.

Figure 3:
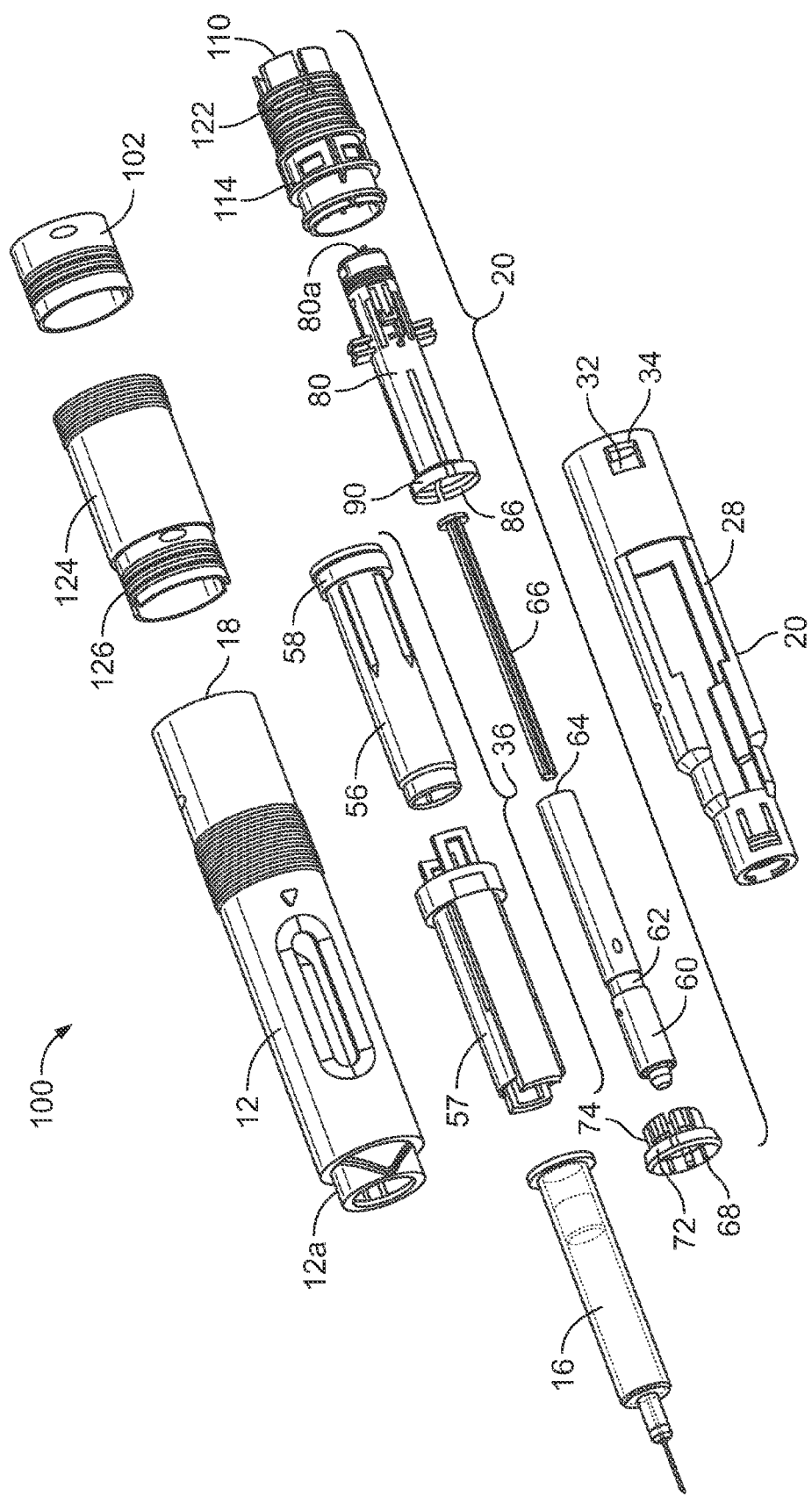
FIG. 3 is a perspective exploded view of the embodiment of FIG. 1 in a disassembled state.
Figure 4:
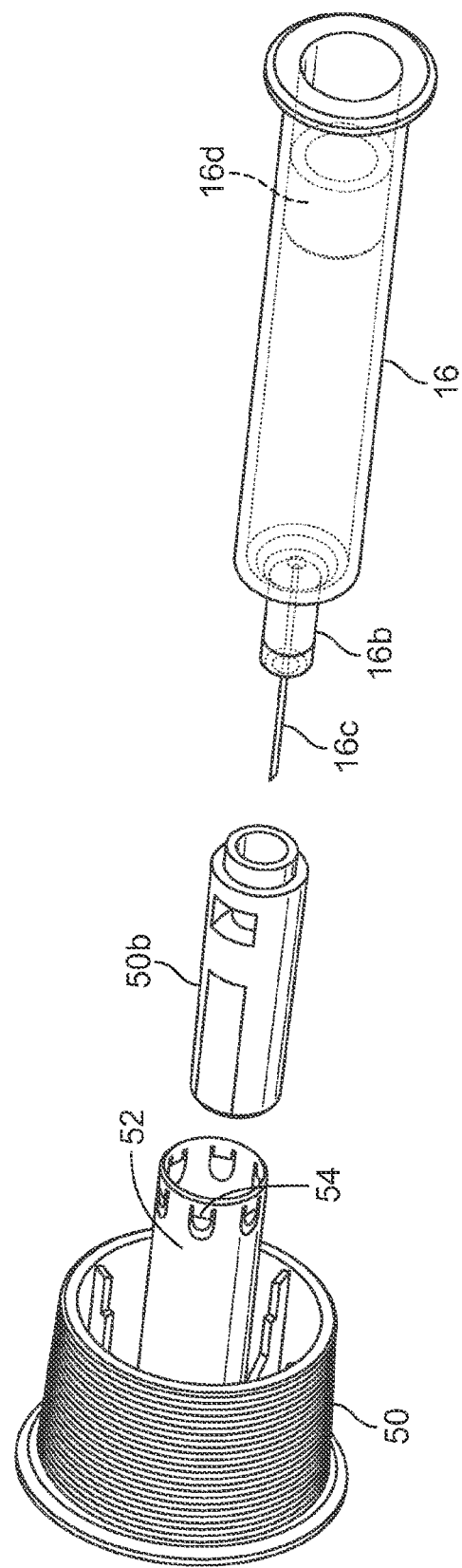
FIG. 4 is a perspective exploded view of a portion of the device of FIG. 1.

A syringe carrier assembly 36, is arranged inside the needle shield 20 and is axially slideable in the proximal direction. The syringe carrier assembly 36 as shown in FIGS. 2-4 comprises an outer body 57 and an inner body 56, both of which are preferably tubular in shape, with the inner body 56 fitting within, and being slideable relative to the outer body 57. The syringe 16 is positioned within the inner body 56 such that there is no relative axial movement between the syringe and the inner body 56. Plunger 60 is in contact with the stopper 16d of the syringe 16. This contact between the plunger 60 and the stopper 16d prevents the syringe 16 from moving in a distal direction. Also prohibiting movement of the syringe 16 within and relative to the inner body is the pointed tongues 54 that is part of the cap assembly 50. These tongues grab the needle protection shield 50b that has attached an RFID tag 202 and assists in holding the syringe 16 in place until cap 50 is removed prior to use of the device. There are no direct attachments or connections between the syringe and the inner body. The proximal end 56c of the inner body 56 is tapered or narrowed to accommodate the proximal end of syringe 16 when it is placed within the inner body 56. The outer body 57 fits over the inner body 56 in a manner that allows relative axial movement between the inner body 56 and the outer body 57.

Because the syringe 16 moves axially with the syringe carrier assembly 36 during the injection process, at some point in that process the syringe carrier assembly 36 will encounter a hard stop 12b on the inside surface of the front body 12 that stops the forward or proximal movement of the assembly 36. In order to prevent damage to the syringe 16 and/or to prevent the phenomenon of kick-back that can be experienced as an undesirable tactile feeling to the person receiving the injection, it is desirable to provide a force dissipation mechanism to minimize or eliminate these possible negative consequences. One such force dissipation mechanism includes a dampener ring 58 that is employed as a third component of this syringe carrier assembly 36. The dampener ring 58 is fitted over the outside surface 56a of the inner body 56 or alternatively fitted into cup portion 57a at the distal end of outer body 57 and abutting distal facing inner lip 57b.

The inner body 56 is also a hollow tube having tapered or narrowing open proximal end 56c that has an internal shape to accept and hold the proximal end of syringe 16 allowing only the staked needle 16c and/or needle hub assembly 16b to protrude proximally from the inner body 56, see FIG. 2. The distal end of the inner body 56 terminates in a flange configuration that has a diameter greater than the outer diameter of the inner body 56. The flange provides a distal bearing surface for abutment with syringe flange and a proximal bearing surface 56h for abutment with the distal bearing surface of the dampener ring 58.

Although the inner body 56 and outer body 57 can move axially relative to each other, the inner and outer bodies are fixed rotationally to each other, i.e., the two bodies cannot rotate relative to each other. As described above, plunger 60 is in contact with the stopper 16d of the syringe 16. This contact between the plunger 60 and the stopper 16d prevents the syringe 16 from moving in a distal direction. Also prohibiting movement of the syringe 16 within and relative to the inner body is the pointed tongues 54 that is part of the cap assembly 50. (see FIG. 4). These tongues grab the needle protection shield 50b and assists in holding the syringe 16 in place until cap 50 is removed prior to use of the device. There are no direct attachments or connections between the syringe and the inner body. The proximal end 56c of the inner body 56 is tapered or narrowed to accommodate the proximal end of syringe 16 when it is placed with the inner body. The outer body 57 fits over the inner body 56 in a manner that allows relative axial movement between the inner body 56 and the outer body 57.

Attached to the staked needle hub 16b that holds needle 16c of syringe 16 is a needle protection shield 50b that is friction fitted to the staked needle hub 16b of the syringe 16. The needle protection shield 50b is surrounded by needle shield grabber 52 having sharp pointed tongues 54 directed somewhat inwards and towards the front or proximal end of the device. The needle shield grabber 52 is operatively connected with cap 50 such that removal of cap 50 results in simultaneous removal of needle protection shield 50b and grabber 52.

The needle shield 50b is typically added to the stacked needle hub 16b by the manufacture of the medicament container, typically a syringe manufacture, as part of the pre-filled syringe manufacturing process prior to the medicament container being filled with the medicament. In addition to fabricating the actual container (glass or plastic), the syringe manufacturer will also be responsible for attaching (staking) needle 16c to hub 16b and also for forming siliconization of the inside of the syringe. Of course, prior to this manufacturing step, the needle shield assembly must be fabricated, as discussed, below in more detail. The fabricator of the needle shield assembly of the invention will combine the RFID tag with the material used to form the needle shield. At this early point in the overall injection device manufacturing process, the RFID tag is capable of storing data that will allow historical tracking. The syringe manufacture will receive the RFID tag enabled needle shield assemblies and needle cannula from another manufacture and will combine these two components as part of the syringe manufacturing process. Again, at this point, the RFID tag can store information inputted by the syringe manufacturer that relates to the cannula source, such as dates, lot numbers, cannula manufacturer identification, locations, etc. As mentioned, the syringe manufacturer can also add data to the RFID relating to siliconization parameters, dates, formulas, testing criteria, etc. Once complete, the syringe with the needle shield assembly is then transferred directly to a medicament filling location or stored/warehoused until shipped to a filling location. Again, data can be written to or read from the RFID tag to track and/or record information relating to the product history.

The medicament filling process is typically performed by another manufacturer, namely a pharmaceutical company or a contract filling company. Again, because the RFID needle shield is attached to the syringe prior to medicament filling, the filling manufacturer can read and write information to the RFID tag relating to medicament, i.e., lot numbers, dates of manufacturing, warnings, safety information, instructions for use, dose limitations, etc. By including the RFID tag as part of the needle shield assembly, this allows tracking and data collection very early in the overall manufacturing process of the complete injection device. Because the needle shield assembly remains on the syringe up until the moment a user of the complete injection device performs the injection, the RFID tag is capable of storing data relating to almost the complete history of injection device. Typically, there are many parties involved in the component and manufacturing processes that result in a finished injection device. These various parties also typically are located in many different physical locations. These parties can include the following:

Rubber Manufacturer
Needle Manufacturer
Needle-Shield Manufacturer
Syringe Manufacturer (Glass/Plastics)
Pharmaceutical Company (drug manufacturer)
Contract Manufacturing Operator (drug filling)
Device Manufacturer (device assembly)
Distribution and shipping Each of the above parties may have different quality and product specific criteria that they control individually and which they document independently from the other parties. Once the syringe has been filled with medicament it is then stored or shipped directly to a location where it is eventually incorporated into a completed injection device. Again, information can be read from or written to the RFID tag relating to storage and shipment of the pre-filled syringe.

The injection device assembly process typically joins or marries the pre-filled syringe with the RFID tag enabled needle shield with the various metal or plastic components that form the working parts of injection device, i.e. dose mechanism, and that cause the medicament in the syringe to be forced through the needle 16c. During the device assembly step data can be written to and/or read from the RFID tag. Additionally, a second RFID tag may accompany one or more components of the dose mechanism. This second RFID tag would contain historical data relating to the manufacture of these components. Once the pre-filled syringe was incorporated with the dose mechanism data on each of the RFID tags could be exchanged thus ensuring that each RFID tag contained the complete product history for a completed injection device.

Figure 5:
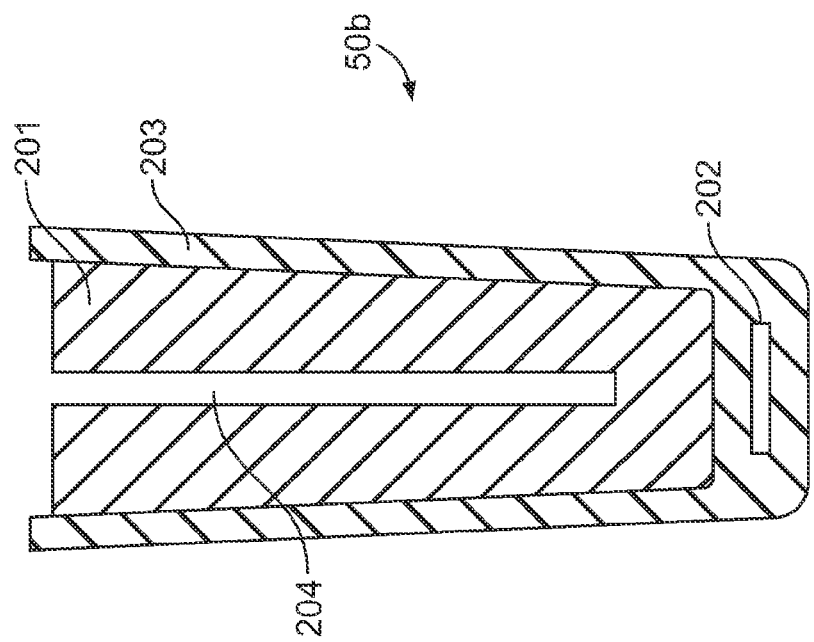
FIG. 5 is a cross-sectional view of a schematic representation of an embodiment of the RFID tag enabled needle shield assembly of the present disclosure.

FIG. 5 illustrates one possible needle shield design that comprises a rigid sheath 203 surrounding and enclosing a flexible needle sheath 201 that is made from a material that is softer than the material used to fabricate the rigid sheath 203. Preferably, the flexible needle sheath 201 comprises a rubber material, however, any material can be used that will allow the injection needle 16c to fit within cavity 204 maintaining sterility and creating a liquid seal with the injection needle. Preferably, the sharp proximal end of the needle 16c is embedded into the proximal end of cavity 204 and into the flexible needle sheath material. The flexible needle sheath 201 can be friction fitted within the rigid sheath or alternatively held in place with an adhesive or other connection means.

Figure 6:
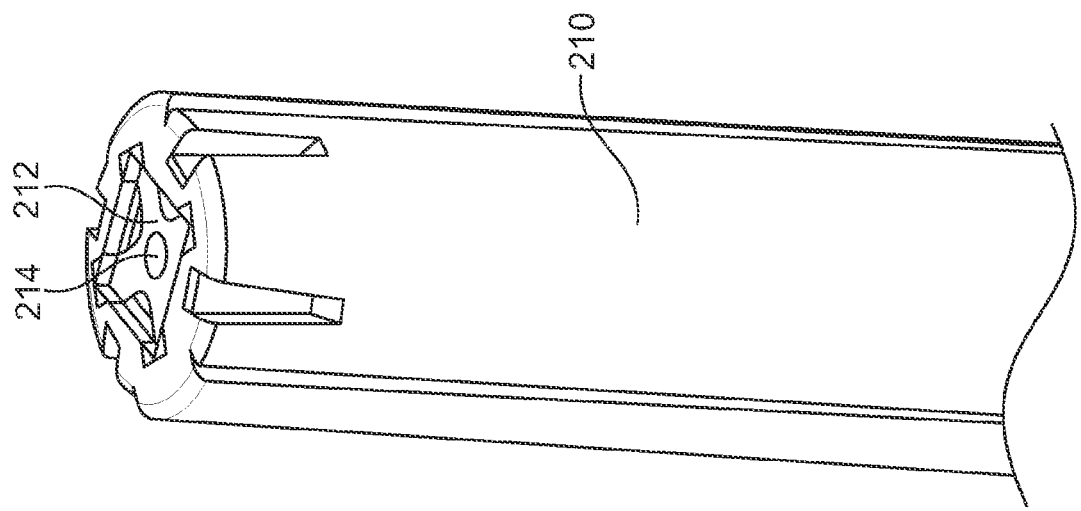
FIG. 6 is a perspective view of mold core pin that could be used manufacture an embodiment of the RFID tag enabled needle shield assembly of the present disclosure.

In the embodiment shown in FIG. 5 an RFID tag 202 is embedded in the proximal end of the rigid shield 203. This can be achieved through a co-molding manufacturing process. In one possible manufacturing process a core pin 210 (see FIG. 6) is used to support the RFID tag 202 while molten plastic material is used to form the rigid sheath 203 and to encapsulate the RFID tag 202. One or more support pillars 214 are located within the pin cavity or cage 212 to support the RFID tag to prevent bending or cracking of the RFID tag during the molding process. One or more robotic tools are used to select, write data, and place the RFID tag in position for the co-molding process. Other robotic tools are used to remove the co-molded RFID tag enabled needle sheath from the fabrication process.

Figure 9:
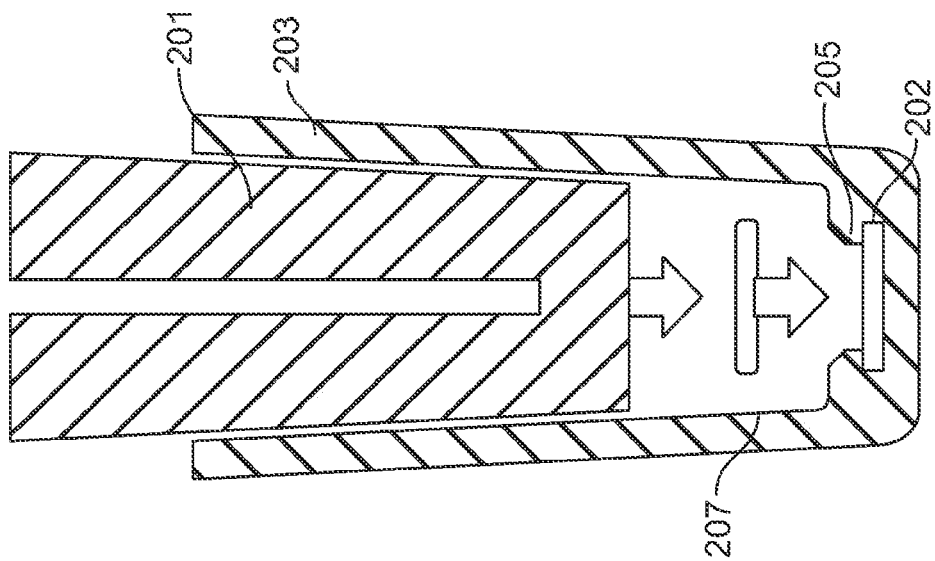
FIG. 9 is a cross-sectional view of a schematic representation of an embodiment of the RFID tag enabled needle shield assembly of the present disclosure.
Figure 8:
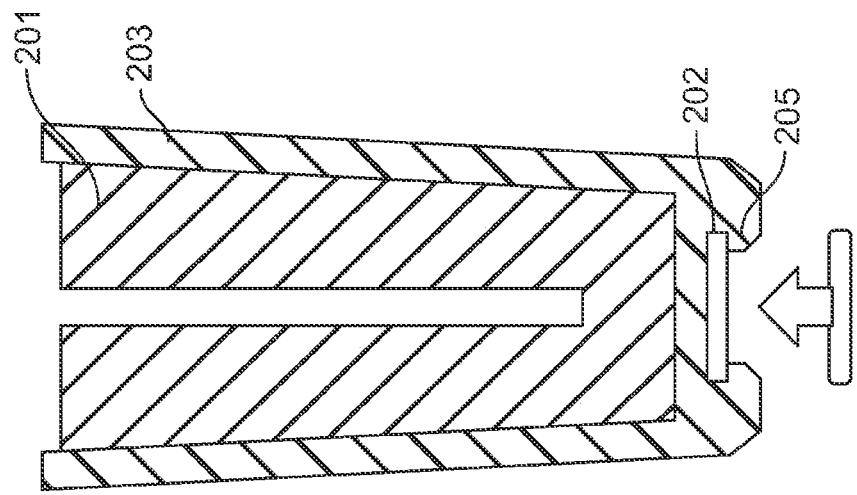
FIG. 8 is a cross-sectional view of a schematic representation of an embodiment of the RFID tag enabled needle shield assembly of the present disclosure.
Figure 7:
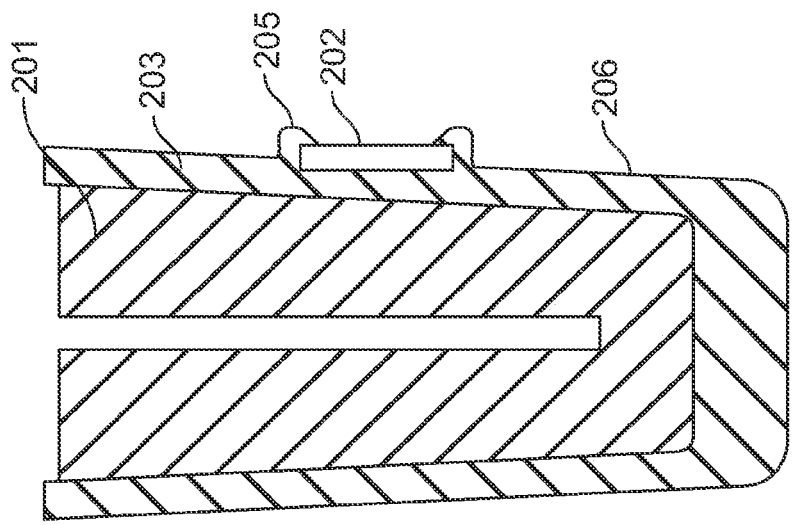
FIG. 7 is a cross-sectional view of a schematic representation of an embodiment of the RFID tag enabled needle shield assembly of the present disclosure.

FIGS. 7-9 show alternative manufacturing techniques to incorporate into or associate the RFID tag 202 with rigid sheath 203, each of which uses a snap-in feature 205, where the RFID tag is held in place with flexible arms, fingers, or channels that are integrally formed in an outside surface 206 or an inside surface 207 of rigid sheath 203. FIG. 9 in particular illustrates that the fitting of the flexible needle sheath 201 within the rigid sheath 203 can be used as ram to seat the RFID tag 202 into snap fittings 205. Although FIGS. 7-9 illustrate the use of both a rigid sheath and a flexible needle sheath as two separate components, it is within the scope of the present invention to incorporate the RFID tag into a needle shield component that is fabricated as a single component, i.e., where the rigid outer portion is integral with a soft flexible inner portion that is capable of sealing the proximal end of the injection needle. Such a single component needle shield that provides both a rigid and a soft needle sheath could be fabricated as individual portions of different hardness materials and then physically and permanently attaching two distinct portions together. It may also be possible to form the single component needle shield by a co-molding process. In this way only a single needle shield need be manufactured as opposed to manufacturing two separate and different components that must then be first assembled together prior to assembling the needle shield assembly to the syringe and injection needle.

Yet another alternative design of the needle shield assembly 50b incorporates an antenna feature. Two possible embodiments are shown in FIGS. 10 & 11 where an antenna 208 is attached and formed around the outside surface of rigid sheath 203 or alternatively printed on the surface of the sheath. In either case the antenna is electrically connected to the RFID tag 202. The use of the antenna will improve both the writing and reading of the RFID tag, especially when the RFID tag is embedded and covered during a co-molding manufacturing process. FIG. 12 shows the antenna feature connected to the RFID tag prior to the antenna being bent or formed around the outside surface of the rigid sheath. An adhesive or coating can be used to hold the antenna 208 to the surface of the rigid sheath.

The RFID tag can be a read only device, but more preferably it is a read-write RFID. The RFID tag can be based in different frequency bands, including those that work in HF-RFID and NFC frequency or UHF frequency. The interaction and reading of the information takes place with industrial RFiD readers for UHF/HF frequency, handheld readers and accessories and common smartphones that implement NFC Technology.

The RFID has a memory that can be read and/or written to using an RFID reader and similar devices. Data stored in the memory is typically separate from a unique identifier, e.g., a serial number, of the RFID tag, which cannot be altered or erased. The storage capacity of the RFID tag should be selected so that it accomplishes the goals of data retention and retrieval, for example, the goal may be to record the entire product history of the device up until the time of use by the end user or it may only need to have memory capacity sufficient to retain information regarding the medicament, such as, dosing and safety information. Higher memory allows RFID tag to store manufacturing data, quality control related information, medicament information, user instructions and any other criteria that allows for a storing of the complete history of the product life cycle. In general, the memory of each RFID tag attached to each needle shield assembly should be sufficient to store data collected at the different points in the product life cycle.

Predefined information will be transformed to a set of data that is then wirelessly transferred to each RFID tag at the outset of the product life cycle. In some cases, it may be possible and desirable to perform a "bulk" transfer of data to a tray full of needle shield assemblies, each having an attached RFID tag. Data transfer on an individual basis could be accomplished by the above-mentioned robotic tool as the needle sheath is removed from the co-molding or RFID attachment process. Bulk transfer of information to a number of RFID tag enabled needle sheaths could occur during medicament filling process or during actual device assembly. As such, in each of the manufacturing and/or assembly steps, e.g. syringe manufacturing, syringe filling, shipping, device assembly, etc., individual item related information will be written to the individual RFID tags or written in "bulk" to a number of RFID tags in an assembled lot. Preferably, the written data is secured and protected through known data security techniques, such as, encryption.

Considering the number of possible designs that injection devices may embody, it is likely that the medicament holding container, e.g., a prefilled syringe, will have a separate manufacturing route compared to that of the main housing injection device that holds the dose delivery mechanism. Late in the device assembly process the two parts, medicament container with the RFID tag and the dose delivery mechanism, are eventually joined to form the complete injection device. In such cases, it is desirable to employ a second RFID tag attached to the main housing of the dose delivery mechanism or to a component within the housing such that a record of the dose delivery mechanism can be tracked and traced independent of the manufacturing and testing of the medicament container that contains the needle shield assembly with the RFID tag. Once the two RFID tags become part of a single device assembly, the data can then be read from each RFID tag or the data can be transferred from one RFID tag to the other. Data exchange between the two RFID tags becomes important because if a problem occurs during injection or after a first injection is performed it is likely that the needle sheath has been removed and disposed of, thus making product life cycle data recovery impossible. However, because data is exchanged between the RFID tag in the needle sheath with the second RFID tag in the device, data can still be recovered in the event the needle shield is no longer available. Since data was transferred from the RFID tag on the needle shield assembly to the RFID tag of the dose delivery mechanism then the complete device history will be available if needed in a post-use quality control or failure analysis.

Figure 13:
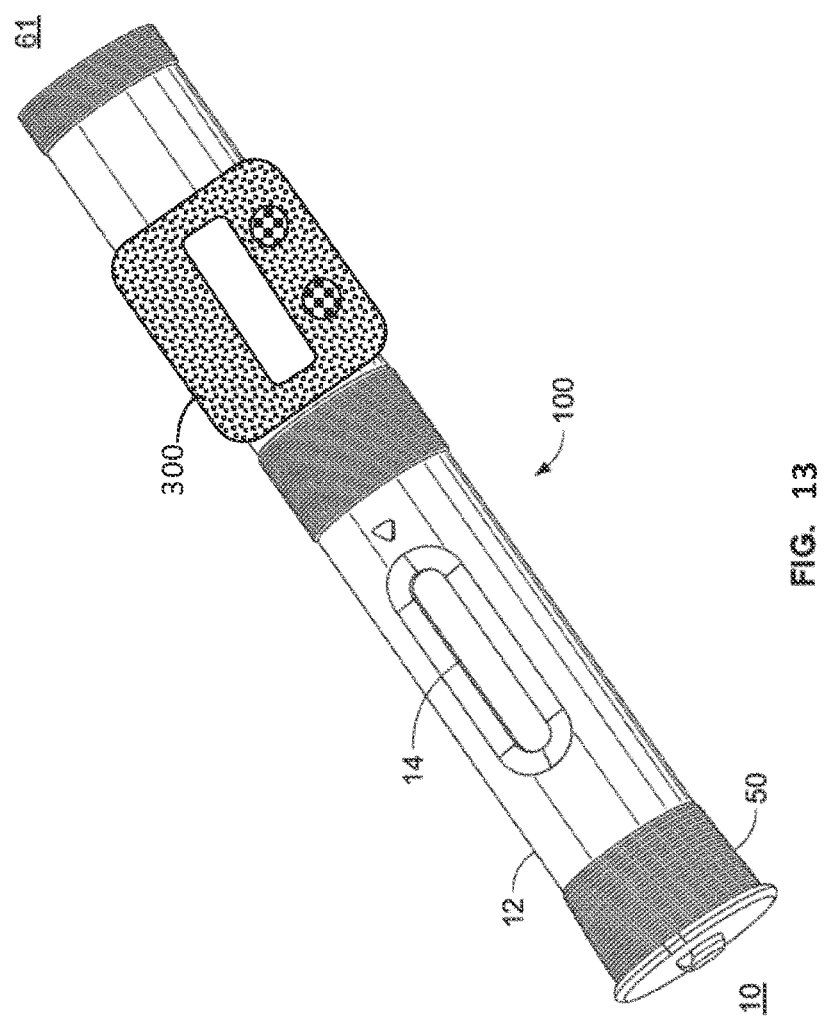
FIG. 13 is a perspective view of the drug delivery device of FIG. 1 having attached thereto a device accessory.

Yet a further possibility includes the use of an injection device accessory 300 (see FIG. 13), such as a so-called loyalty sleeve that is attached to the injection device by the end user or health care provider and contains information specific to the user. The accessory can be attached directly to the outer surface of the injection device and can be configured to acquire information directly from the RFID tag associated with either the needle shield assembly, injection device, or both. Attachment can be accomplished with a clip-on or snap-on type connector such that it is easily removed and attached to another injection device. The device accessory 300 can include yet another RFID tag, an RFID tag reader, a microprocessor, memory, a display, and/or user interface to input information or control operation of the device accessory, including as buttons or a touch screen. The device accessory 300 can be configured to communicate with an external source, such as, a smart phone, and can track the functioning of the device in actual use. For example, the accessory could acquire and store injection doses and time frequencies of injections. Such information could then be accessed by a health care provider to monitor patient compliance with a treatment regime.

Examples of the types of data that can be stored on one or both of the RFID tags include:
- dimensional properties, siliconization profiles & parameters, unique ID per needle shield assembly;
- Storage of product & quality related data at the drug filling location,
  - e.g. filling date, batch, machine, expiration date, drug identifier for unlabeled syringes;
- Storage of product & quality related data at device manufacturing location, e.g. dimensional properties, components used, unique ID, batch no. for each RFID on the dose delivery mechanism;
- Storage and exchange of product & quality related data at device assembly location, e.g. specific assembly parameters & dates, linking data from the dose delivery mechanism with the needle shield assembly data.

Exchange, check and storage of data at the user level using accessories such as smart phone applications and/or loyalty sleeves attached to the device. The stored user data can be used to analyze the function of device, e.g., injection time analysis, thus tracking product history automatically. Such product history is useful in rapid complaint handling by analyzing a single device throughout the entire supply chain and to assist in product recall and/or consumer warnings using smartphone.

Turning back to the injection device 100, FIG. 2 shows an optimal second RFID tag 220 attached to or embedded in the housing 24. This second RFID can communicate with the RFID associated with the needle shield assembly and with the device accessory 300. FIG. 3 shows the rear part or power unit 20 of the injector according to FIG. 1. It comprises a plunger 60 formed as a tube and with an outer diameter somewhat smaller than the inner diameter of the syringe body to be used. The plunger 60 is arranged with a circumferential groove 62 with a certain width. Inside the plunger 60 a helical compression spring 64 is arranged and inside the spring 64 here is a spring guide 66. Adjacent the groove 62 of the plunger 60 a holding member 68 is arranged. It comprises a ring-shaped body having an annular ledge arranged around its circumference and a number of flexible tongues 74 directed towards the rear or distal end of the power unit. Each tongue 74 is arranged with inwardly directed ledges arranged and shaped as to fit into the groove 62 of the plunger 60. Each tongue 74 is further arranged with reinforcing ribs on the outer surfaces.

Surrounding the plunger 60 is an activator 80 with a mainly tubular shape. Its front or proximal end, to the left in the figures, has an inclined transition surface which meets with a band-shaped part with enlarged diameter. On the inner surface adjacent the transition surface an annular inwardly directed ledge 86 is arranged, with a shape as to fit into the groove 62 of the plunger. A number of longitudinally directed cut-outs are arranged at the front part of the actuator 80 so as to form flexible tongues 90. The activator 80 is further provided with two stop ledges directed radially outwards from the outer surface on either side. The upper end of the activator 80 is arranged with an end wall 80*a*.

Outside the activator 80 is an actuator sleeve 110 is slidably arranged, also of a generally tubular form. It comprises a front end with a conical part ending in a ledge on its outer surface. At a distance from the ledge a first annular ring 114 is arranged the outer surface. A second annular ring is also arranged a further distance from the ledge. The rear end of the actuator sleeve 110 is arranged with two oppositely arranged cut-outs of a generally rectangular shape where the widths correspond to the width of the stop ledges of the actuator 80. A compression spring 122, hereafter named needle shield spring is surrounding the actuator sleeve.

The previously named components of the power unit are housed in a rear housing 124 of a generally tubular shape, where the front end of the rear housing 124 has a somewhat lesser diameter, corresponding to the inner diameter of the rear end of the front body and provided with a number of annular protrusions 126 which are intended to fit into the corresponding annular recesses 18 on the inner surface of the front body 12.

The function of injector 100 described above according to the invention will now be described with respect to the embodiment shown in FIG. 2. When assembling the injector the front and the rear parts are assembled individually. As regards the power unit 20 the plunger 60 is held against the force of the compression spring 64 in that the inwardly directed ledges of the tongues 90 of the activator 80 are situated in the groove 62 of the plunger 60 and that the actuator sleeve 110 prevents the tongues 90 from moving outwards. Further the tongues 74 of the holding member 68 are also arranged in the groove 62. The tongues 90 of the activator 80 are adjacent the tongues 74 as a second safety means should the tongues 90 move out of the groove 62 of the plunger 60.

A syringe 16 is placed in the front end 12 within inner body 56 and rear body 13 is attached to the front body 12 wherein the protrusions 126 fit into the recesses 18. Preferably the syringe 16 is a pre-filled syringe where a medicament is placed within the barrel of the syringe 16 and sealed at the distal end with a slidable stopper or piston 16*d*. The staked needle 16*c* is sealed with the needle protection shield 50*b*, which contains RFID tag 202. The front body 12 and rear body 13 are then connected together. The needle protection cap 50 with needle shield grabber 52 is inserted into the front end of the device. The device is now ready for use.

When an injection is to be performed the needle protection cap 50 and attached grabber 54 is pulled out of the injector carrying with it the needle protection shield 50*b* along with RFID tag 202. This causes the sharp pointed tongues 54 to be pushed into the rubber needle protection shield 50*b* and remove it from the needle hub 16*b*. The front end of the injector is then pressed against the injection site and the somewhat projecting front end of the needle shield 20 is pushed into the housing 124 against the force of the compression spring 122 acting between the second annular ring of the actuator sleeve and a ledge arranged on the actuator 80. The upper end of the needle shield 20 is in contact with the first annular ring 114 of the actuator sleeve 110 and its movement causes the actuator sleeve 110 to move backwards or distally whereby a part of the band-shaped part is situated outside the front part of the actuator sleeve 110.

In the embodiment shown in FIG. 2 that does not include a distal activation button, the device is activated when the needle shield 20 is pushed against an injection site causing it to retract into the housing 12 in the distal direction. Once fully retracted, the actuator sleeve 110 will release activator 80 causing the spring 64 to release, firing the device and initiating the injection sequence.

The force of the compression spring 64 urges the plunger 60 to push on the stopper 16d of the syringe. But because of the friction between stopper 16d and syringe barrel inner wall and the incompressibility of the liquid medicament in the syringe and the very small flow passage through the needle, the force will push the syringe 16 and the syringe assembly 36 forward proximally, where needle 16c will penetrate the skin of the patient. The penetration stops when the syringe carrier assembly abuts and contacts the hard stop 12b. Although the outer body 57 encounters the hard stop 12b inside the front body 12 stopping its forward motion, the inner body 56 and the syringe 16 continue to move slightly axially forward (proximally) relative to the outer body 57. In the case of the syringe carrier assembly 36, the dampener ring 58 absorbs the forward momentum compressing slightly and eventually stopping the inner body 56 and the syringe 16. The compression and energy absorbing characteristics of the dampening ring 58 greatly reduces, if not eliminates, the end of injection negative tactile feel experienced by the person receiving the injection.

The force from the compression spring 64 now moves the stopper 16d inside the syringe and the liquid medicament is injected into the patient until the stopper 16d reaches the inner front end of the syringe barrel. When the plunger has moved this distance, its rear end has passed the ledges of the activator 80 and the tongues 90 are moved inwards. Because the compression spring 64 is also acting on the activator 80, the activator 80 is moved inside the actuator sleeve. Because of this and because the needle shield spring 122 is acting on the actuator sleeve 110 it is urged forward. When now the injector is removed from the injection site, the force of the needle shield spring 122 pushes the actuator sleeve 110 and thus the needle shield 20 connected to it forward, whereby the needle shield 20 is pushed out of the front end of the injector and surrounds the needle 16c. The movement of the actuator sleeve 110 causes the band-shaped part of the actuator 80 to pass ribs arranged on the inner surface of the actuator sleeve 110. These ribs prevent any attempts to push the needle shield 20 back into the injector because the ribs will abut the front end of the band-shaped part of the actuator 80.

It is to be understood that the embodiments described above and in the drawings are to be regarded only as non-limiting examples of the invention and that they may be modified in many ways within the scope of the claims. This application is therefore intended to cover any variations, uses or adaptations of the invention using its general principles. Further, this application is intended to cover such departures from the present disclosure as come within known or customary practice in the art to which this invention pertains.

The invention claimed is:

1. A shield assembly for providing a sterile enclosure of an outlet fixedly attached to a container of medicament positioned within a medicament delivery device, the shield assembly comprising:
   a rigid sheath configured to fit within, be surrounded by, and operatively engaged with a grabber that is axially fixed to a protective cap connected to a proximal end of a medicament delivery device such that removal of the protective cap from the medicament delivery device causes the grabber to remove the shield assembly from the container of medicament;
   a flexible sheath positioned within the rigid sheath and surrounding the outlet of the container of medicament; and
   an RFID tag fixedly positioned between the flexible sheath and the rigid sheath and not attached to the protective cap.

2. The shield assembly of claim 1, wherein the flexible sheath has an outside surface and the rigid sheath has an inside surface, where the RFID tag is positioned between the outside surface and the inside surface.

3. The shield assembly of claim 1, wherein the flexible sheath abuts the RFID tag positioned on an inside surface of the rigid sheath.

4. The shield assembly of claim 1, wherein the RFID tag is read-write tag.

5. The shield assembly of claim 4, where the RFID tag further comprises a read-only memory that contains product identification data.

6. The shield assembly of claim 1, wherein the rigid sheath is attached to the flexible sheath such that axial movement of rigid sheath causes axial movement of the flexible sheath and the RFID tag.

7. The shield assembly of claim 1, wherein the RFID tag is fixedly attached to an inside surface of the rigid sheath.

8. The shield assembly of claim 7 wherein the RFID tag is fixedly attached by one of a snap fit, an inlay, co-molded, an adhesive, lamination, paid, a press fit or a combination thereof.

9. The shield assembly of claim 1, further comprising an antenna in electrical communication with the RFID tag.

10. The shield assembly of claim 9, wherein the antenna is positioned on an outside surface of the rigid sheath.

11. The shield assembly of claim 1, wherein the flexible sheath is permanently attached to an inside surface of the rigid sheath.

12. The shield assembly of claim 1, wherein the flexible sheath has an interior portion comprising a material that forms a sterile and fluid tight seal with the outlet of the container of medicament.

13. The shield assembly of claim 12, wherein the outlet comprises an injection needle.

14. A system comprising:
   the shield assembly of claim 1; and
   a device accessory that is configured to read data from an RFID tag.

* * * * *